United States Patent
Kuninaka et al.

(10) Patent No.: US 7,038,203 B2
(45) Date of Patent: May 2, 2006

(54) METHOD FOR OBSERVING HIGH-ALTITUDE NEUTRAL AIR AND DEVICE FOR OBSERVING HIGH-ALTITUDE NEUTRAL AIR

(75) Inventors: Hitoshi Kuninaka, Kawasaki (JP); Yoshiki Yamagiwa, Hamamatsu (JP)

(73) Assignee: Japan Aerospace Exploration Agency, Tokyo (JP)

( * ) Notice: Subject to any disclaimer, the term of this patent is extended or adjusted under 35 U.S.C. 154(b) by 24 days.

(21) Appl. No.: 10/759,009

(22) Filed: Jan. 20, 2004

(65) Prior Publication Data

US 2004/0144921 A1    Jul. 29, 2004

(30) Foreign Application Priority Data

Jan. 24, 2003   (JP)   ............... 2003-015829

(51) Int. Cl.
    B64G 1/36       (2006.01)
(52) U.S. Cl. ............... 250/309; 250/251; 250/427; 376/130
(58) Field of Classification Search ............... 250/251, 250/309, 382, 374, 375, 379, 393, 395, 281–283, 250/286–288, 299, 291–298, 300, 427; 376/130
    See application file for complete search history.

(56) References Cited

U.S. PATENT DOCUMENTS

| | | | | |
|---|---|---|---|---|
| 3,207,895 A | * | 9/1965 | Schumacher | 250/380 |
| 3,657,542 A | * | 4/1972 | Futch et al. | 250/251 |
| 3,742,219 A | * | 6/1973 | Damm et al. | 250/251 |
| 3,757,114 A | * | 9/1973 | Simms et al. | 250/251 |
| 3,767,925 A | * | 10/1973 | Foley et al. | 250/251 |
| 3,790,411 A | * | 2/1974 | Simms et al. | 438/516 |
| 4,053,776 A | * | 10/1977 | Hertzberg et al. | 250/382 |
| 4,349,505 A | * | 9/1982 | Stirling | 376/130 |
| 4,434,131 A | * | 2/1984 | Dagenhart et al. | 376/130 |
| 4,439,395 A | * | 3/1984 | Kim | 376/130 |
| 4,486,665 A | * | 12/1984 | Leung et al. | 250/427 |
| 4,559,477 A | * | 12/1985 | Leung et al. | 315/111.81 |
| 6,069,362 A | * | 5/2000 | Giakos | 250/394 |
| 6,541,769 B1 | * | 4/2003 | Takada et al. | 250/290 |
| 6,573,510 B1 | * | 6/2003 | Vella | 250/423 R |
| 6,762,407 B1 | * | 7/2004 | Kalinitchenko | 250/294 |
| 2003/0155496 A1 | * | 8/2003 | Kalinitchenko | 250/281 |
| 2004/0144921 A1 | * | 7/2004 | Kuninaka et al. | 250/309 |

OTHER PUBLICATIONS

CSS, "Space Instruments", http://utd500.utdallas.edu/www_root/documents/Spaceinstruments.htm.*

(Continued)

*Primary Examiner*—John R. Lee
*Assistant Examiner*—Bernard E. Souw
(74) *Attorney, Agent, or Firm*—Oliff & Berridge, PLC

(57) ABSTRACT

Ion particles are discharged so as to be influenced by a magnetic field originated from the earth, and collided with high-altitude neutral air to generate high velocity neutral particles through charge exchange. The high velocity neutral particles are analyzed. The distance to the high-altitude neutral air from at least one of the discharging positions of the ion particles and the measured positions of the high velocity neutral particles is determined based upon the period of time between the discharging time of the ion particles and the time the high velocity neutral particles are analyzed. Moreover, the direction of the high-altitude neutral air is determined by measuring the direction of the high velocity neutral particles. In addition, the spatial position of the high-altitude neutral air is determined based upon the measured direction of the high velocity neutral particles.

14 Claims, 1 Drawing Sheet

OTHER PUBLICATIONS

NWM, "Neutral Wind Meter", http://129.110.7.63/heelis/nwmf.html.*
NASA "9. Trapped Radiation", http://www-istp.gsfc.nasa.gov/Education/wtrap1.html.*
"The Solar Wind Interaction with Venus and Mars: Energetic Neutral Atom and X-Ray imaging", http://www.ava.fmi.fi/~kallio/Manuscript-No24/ASR_24_venusmars3_Final.pdf.*
ASPERA-3 Flight Performance Report, http://www.aspera-3.org/ASPERA_Science.pdf.*
Neutral Wind Monitor (NWM), http://www.vs.afrl.mil/TechProgs/CNOFS/NWM.html.*
"Coupled Ion-Neutral Dynamics Investigation", http://129.110.7.63/heelis/factsheet.pdf.*
"Lower Temperature Coupling Studies", http://www.haystack.mit.edu/mhrobs/emphasis/science3.pdf.*
NRA-03-OSS-01, "Sun-Earth Connection Instrument Development Program", http://research.hq.nasa.gov/code_s/nra/current/NRA-03-OSS-01-SECID/winners.html.*
Lilensten et al., "On the fast movements of the thermosphere", Ann. Geophysicae 18, 2001, 1651-1656.*
Collier et al., "Observation of neutral atoms from the solar wind", J. Geophys. res. 106 (A11), 2001, 24,893-24,906.*
R.A. Heelis, "Sensor Development Thermospheric Neutral Wind Measurements", Scientific Report No. 2, May 15, 2002, AFRL-VS-TR-2003-1555.*
R.A. Heelis, "Sensor Development Thermospheric Neutral Wind Measurements", Final Report, Nov. 15, 2003, AFRL-VS-HA-TR-2004-1028.*
S. Grahn et al., "Astrid—An attempt to make the microsatellite a useful tool for space science", Proceedings of the 11th Annual AIAA/USU Conference on Small Satellites, 1995, XP009029828, pp. 1-11, Logan, Utah.
H.D. Voss et al., "Satellite observations and instrumentation for measuring energetic neutral atoms", Optical Engineering, vol. 32, No. 12, 1993, XP009029841, pp. 3083-3089.
Wehr et al., "Calibration and first results of stellar occulation measurements with GOMOS on envisat", Proceedings of IEEE International Geoscience and Remote Sensing Symposium Igarss 2002, Toronto, Ontario, Canada, vol. 1, Jun. 24, 2002, pp. 605-607, XP010597418.

* cited by examiner

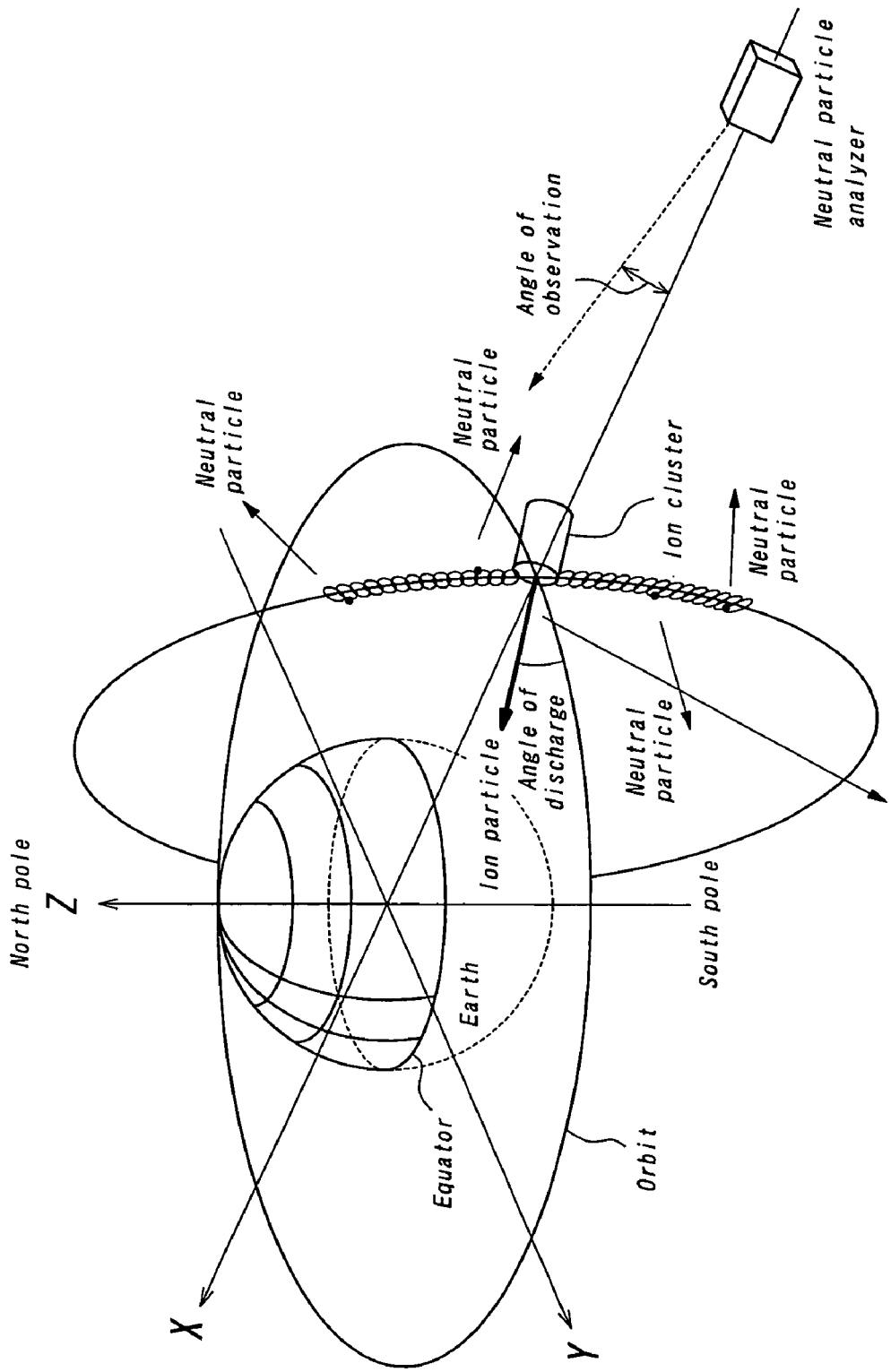

METHOD FOR OBSERVING HIGH-ALTITUDE NEUTRAL AIR AND DEVICE FOR OBSERVING HIGH-ALTITUDE NEUTRAL AIR

BACKGROUND OF THE INVENTION

1. Field of the Invention

This invention relates to a method for observing high-altitude neutral air and a device for observing high-altitude neutral air which are usable in space operational business enterprise and space weather forecast business enterprise.

2. Description of the Related Art

Data concerning high-altitude neutral air is very important because the orbital altitude of a space satellite may decay due to the atmosphere drag in the high-altitude neutral air and the reentry of the space satellite into the atmosphere can be predicted from the high-altitude neutral air data.

In a conventional observation for the high-altitude neutral air, an observing instrument is mounted on a space satellite, which is disposed in the high-altitude neutral air. As a result, since the observing instrument is positioned in a given area of the high-altitude neutral air, the observation for the high-altitude neutral air is carried out at every area where the observing instrument is positioned.

Since the observing area is contaminated by positioning the space satellite, with the conventional technique, the high-altitude neutral air can not be observed precisely. Moreover, with the conventional technique, only the data concerning a given area of the high-altitude neutral air by positioning the observing instrument in the given area can be obtained, so the total data concerning the high-altitude neutral air can not be obtained simultaneously.

The data concerning the high-altitude neutral air can be obtained from the Jacchia model (Standard Jacchia Reference Atmosphere 1977) which is a simulated and modeled distribution of high-altitude neutral air based on the changes in altitude of many previously launched space satellites. Since the predictive accuracy of the Jacchia model is poor, it can not be employed in a technical field requiring prompt response and accuracy such as the prediction of the reentry of a space satellite.

SUMMARY OF THE INVENTION

It is an object of the present invention to observe the high-altitude neutral air widely and precisely.

A method for observing high-altitude neutral air comprises the steps of:

discharging ion particles so as to be influenced by magnetic field lines of the earth, colliding the ion particles with high-altitude neutral air to generate high velocity neutral particles through charge exchange, and detecting the high velocity neutral particles, determining the distance to the high-altitude neutral air from at least one of the discharge position of the ion particles and the detected position of the high velocity neutral particles based on the period of time between the discharge of the ion particles and the detection of the high velocity neutral particles, thereby determining both the direction of the high-altitude neutral air based on the direction of the high velocity neutral particles and the spatial position of the high-altitude neutral air.

In an exemplary embodiment, a given ion source is disposed in earth orbit and ion particles are then discharged from the ion source so as to be influenced by the magnetic field lines of the earth. When the ion particles collide with the high-altitude neutral air, high velocity neutral particles are generated through charge exchange with the ion particles. The high velocity neutral particles travel inertially without being disturbed by the magnetic field lines of the earth, and are detected with a neutral particle analyzer disposed in the orbit around the earth.

The discharge velocity of the ion particles can be predetermined, and the velocity of the neutral particles can be measured with the neutral particle analyzer. Moreover, the relative position between the ion source and the neutral particle analyzer can be predetermined, and the discharging angles of the ion particles from the ion source as well as the observing angle of the neutral particle analyzer can also be predetermined. Therefore, if the period of time between the discharge of the ion particles and the detection of the neutral particles is measured, at least one of the distances between the high-altitude neutral air and the ion source and between the high-altitude neutral air and the neutral particle analyzer can be determined.

Moreover, since the neutral particles can be detected with the neutral particle analyzer, the direction of the high-altitude neutral air can be determined from the detected direction of the neutral particles.

Furthermore, based upon the distances and the direction of the high-altitude neutral air as measured above, the spatial position of the high-altitude neutral air can be determined.

Herein, the wording "high-altitude neutral air" means an atmosphere within an altitude range of about 100 km–1000 km.

Also, the wording "charge exchange" means a reaction where an ion particle "A" is collided with an ion particle "B", causing the charge transfer of the ion particle "A" to the ion particle "B" and thus, generating a high velocity neutral particle "A" and a high velocity neutral particle "B" (A*+B→A+B*).

Furthermore, high velocity neutral particles may be generated from the charge exchange with the ion particles in the high-altitude neutral air. By measuring the detection frequency of the neutral particles, the particle density of the high-altitude neutral density may be determined.

If the ion particles are made of the same particles as the neutral particles, the energy of the ion particles and the energy of the neutral particles before and after their collision may be conserved. Therefore, the kinetic energy of the neutral particles is equal to the kinetic energy of the ion particles. In contrast, if the ion particles are made of different particles from the neutral particles, the kinetic energy of the neutral particles is increased or decreased based on the differences in ionization voltage between the ion particles and the neutral particles before and after their collision.

Since the composition of the ion particles are known, if the change in kinetic energy of the ion particles is measured, the composition of particles in the high-altitude neutral air can be determined, and thus, the composition of the high-altitude neutral air can be determined.

It is desired that the ion particles are comprised of particles which rarely exist on the high and low orbits of the earth. In this case, the ion particles can be recognized clearly against other particles in the space. Concretely, the ion particles may be made of krypton particles or xenon particles.

The ion particles may be discharged in pulse or modulation. In this case, the discharging time of the ion particles and the time of measurement of the high velocity neutral particles can be recognized clearly, and the distance for the high-altitude neutral air can be measured easily and precisely.

The spatial position, the density and the composition of the high-altitude neutral air may be determined precisely. By controlling the discharge angle of the ion particles from the ion source and the observing angle of the neutral particle analyzer, the density and the composition of the high-altitude neutral air can be widely determined in a short period of time.

BRIEF DESCRIPTION OF THE DRAWINGS

For better understanding of the present invention, reference is made to the attached drawings, wherein FIG. 1 is an explanatory view relating to a method for observing high-altitude neutral air according to the present invention.

DESCRIPTION OF THE PREFERRED EMBODIMENTS

This invention will be described in detail with reference to the accompanying drawings.

FIG. 1 is an exemplary method for observing high-altitude neutral air according to the present invention.

In FIG. 1, an ion cluster source is disposed as an ion source on the orbit above the equator of the earth, and a neutral particle analyzer is disposed in the rear side of the ion cluster source. Ion particles are discharged from the ion cluster source, and are influenced by the magnetic field lines generated from the axis of the earth. In this case, the ion particles are rotated along the magnetic field lines, which is defined as "Larmor motion", and moved north and south. If a given condition is satisfied, the mirror confining mechanism is generated, so that the ion particles are moved repeatedly north and south.

Ion particles collide with inner particles in the high-altitude neutral air (not shown) at the black points in FIG. 1, causing the charge transfer of the ion particles to the inner particles and thus, generating neutral particles in the directions designated by the arrows. The neutral particles travel inertially at their respective high velocities without the disturbance of the magnetic field lines, and are detected with the neutral particle analyzer.

The discharge velocity of the ion particles can be predetermined, and the velocity of the neutral particles can be measured with the neutral particle analyzer. Furthermore, the relative position between the ion cluster source and the neutral particle analyzer can be predetermined. In addition, the discharge angle of the ion particles from the ion cluster source can be predetermined and the observing angle of the neutral particle analyzer can be predetermined. Therefore, if the period of time between the discharging of the ion particles and the detection of the neutral particles is measured, at least one of the distances between either the high-altitude neutral air and the ion cluster source, and between the high-altitude neutral air and the neutral particle analyzer can be determined.

The direction of the high-altitude neutral air can be determined from the detected direction of the neutral particles using the neutral particle analyzer.

As mentioned above, it is desired that the ion particles are made of particles which rarely exist on the orbit of the earth such as krypton particles or xenon particles in order to be distinguished from other particles in nature. In order to enhance the easiness and precision of the measurement of the distance for the high-altitude neutral air, the ion particles may be discharged in pulse or modulation.

If the detection frequency of the neutral particles is measured with the neutral particle analyzer, the particle density of the high-altitude neutral air can be determined. Because the composition of the ion particles is known, by measuring the changes in kinetic energy of the neutral particles, the composition of the high-altitude neutral air can be determined based upon the fact that changes in kinetic energy of the neutral particles depend on the specific composition of particles in the high-altitude neutral air.

Because it is not required that the ion cluster source and the neutral particle analyzer be disposed directly in the high-altitude neutral air, the spatial position, the density and the composition of the high-altitude neutral air can be precisely determined without contamination from, for example, the ion cluster source and the neutral particle analyzer. Moreover, if the discharge angle of the ion particles from the ion cluster source and the observing angle of the neutral particle analyzer is controlled, the density and the composition of the high-altitude neutral air can be determined widely in a short period of time.

The ion cluster source and the neutral particle analyzer may be mounted on a space satellite disposed in an earth orbit. In this exemplary embodiment, the position of the space satellite may be adjusted so as to position the ion cluster source and the neutral particle analyzer as illustrated in FIG. 1. The ion cluster source and the neutral particle analyzer may be mounted on the same space satellite or different space satellites. In the latter case, since the degree of freedom in disposition of the ion cluster source and the neutral particle analyzer may be increased, the high-altitude neutral air may be observed and measured more widely.

Although the present invention was described in detail with reference to the above examples, this invention is not limited to the above disclosure and every kind of variation and modification may be made without departing from the scope of the present invention.

In summary, since it is not required that the ion source and the neutral particle analyzer are disposed directly in the high-altitude neutral air, the spatial position, the density and the composition of the high-altitude neutral air may be precisely determined. Moreover, when the discharge angle of the ion particles from the ion source and the observing angle of the neutral particle analyzer are appropriately controlled, the density and the composition of the high-altitude neutral air may be determined widely in a short period of time.

What is claimed is:

1. A method for observing high-altitude neutral air, comprising the steps of:

discharging ion particles so as to be influenced by a magnetic field originated from the earth, colliding said ion particles with high-altitude neutral air to generate high velocity neutral particles through charge exchange, and detecting said high velocity neutral particles to determine the distance to said high-altitude neutral air from at least one of the discharging positions of said ion particles and the detected positions of said high velocity neutral particles from the period of time between the time of discharge of said ion particles and the time of detecting said high velocity neutral particles, to determine the moving direction of said high-altitude neutral air from the detected direction of said high velocity neutral particles, and to determine the spatial position of said high-altitude neutral air, wherein the relative position between the discharging position of the ion particles and the detected positions of the neutral particles is not predetermined.

2. The observing method as defined in claim 1, wherein the density of said high-altitude neutral air is determined by the detection frequency of said high velocity neutral particles.

3. The observing method as defined in claim 1, wherein the composition of said high-altitude neutral air is determined by measuring the changes in kinetic energy of said high velocity neutral particles.

4. The observing method as defined in claim 1, wherein said ion particles comprise at least one of krypton particles and xenon particles.

5. The observing method as defined in claim 1, wherein said ion particles are discharged in pulses.

6. The observing method as defined in claim 1, wherein the discharge of said ion particles is modulated.

7. A device for observing high-altitude neutral air, comprising:
   an ion source for discharging ion particles which is disposed on an orbit of the earth, and
   a neutral particle analyzer disposed on an orbit of the earth;
   wherein the relative position between the ion source and the neutral particle analyzer is not predetermined.

8. The observing device as defined in claim 7, wherein said ion source discharges ion particles so as to be influenced by magnetic field lines of the earth.

9. The observing device as defined in claim 8, wherein said ion particles comprise at least one of krypton particles and xenon particles.

10. The observing device as defined in claim 8, wherein said ion particles are discharged in pulses.

11. The observing device as defined in claim 8, wherein the discharge of said ion particles is modulated.

12. The observing device as defined in claim 8, wherein said neutral particle analyzer detects high velocity neutral particles generated as a result of charge exchange between said ion particles and high-altitude neutral air at the time of their collision.

13. The observing device as defined in claim 7, wherein said ion source and said neutral particle analyzer are mounted on the same space satellite.

14. The observing device as defined in claim 7, wherein said ion source and said neutral particle analyzer are mounted on respective difference space satellites.

* * * * *